US008936599B2

(12) United States Patent
Glazer

(10) Patent No.: US 8,936,599 B2
(45) Date of Patent: Jan. 20, 2015

(54) TRANSLATIONAL INSTRUMENTATION FOR SPONDYLOLISTHESIS AND SCOLIOSIS REDUCTION

(75) Inventor: Paul Glazer, Chestnut Hill, MA (US)

(73) Assignee: Tenzin LLC, Chestnut Hill, MA (US)

( * ) Notice: Subject to any disclaimer, the term of this patent is extended or adjusted under 35 U.S.C. 154(b) by 175 days.

(21) Appl. No.: 13/287,811

(22) Filed: Nov. 2, 2011

(65) Prior Publication Data

US 2013/0110113 A1    May 2, 2013

(51) Int. Cl.
 A61B 17/58    (2006.01)
 A61B 17/60    (2006.01)
 A61F 2/00    (2006.01)
 A61B 17/70    (2006.01)

(52) U.S. Cl.
 CPC ................................ *A61B 17/7077* (2013.01)
 USPC ............................................. 606/90; 606/105

(58) Field of Classification Search
 CPC .......................... A61B 17/025; A61B 17/7077
 USPC .................................................. 606/90, 105
 See application file for complete search history.

(56) References Cited

U.S. PATENT DOCUMENTS

| 4,957,495 A * | 9/1990 | Kluger ............................. 606/58 |
| 5,601,556 A * | 2/1997 | Pisharodi ..................... 606/86 A |
| 6,168,601 B1 * | 1/2001 | Martini ............................. 606/90 |
| 6,558,392 B1 * | 5/2003 | Martini ............................. 606/90 |
| 7,744,649 B2 | 6/2010 | Moore |
| 7,811,288 B2 | 10/2010 | Jones et al. |
| 7,988,700 B2 | 8/2011 | Shluzas et al. |
| 8,007,517 B2 | 8/2011 | Lins et al. |
| 2005/0245928 A1 * | 11/2005 | Colleran et al. ................ 606/61 |
| 2007/0191856 A1 * | 8/2007 | Gil et al. .......................... 606/90 |
| 2010/0249792 A1 * | 9/2010 | Bonvallet et al. ............... 606/90 |
| 2010/0274252 A1 * | 10/2010 | Bottomley et al. ............. 606/90 |

* cited by examiner

*Primary Examiner* — David Bates
(74) *Attorney, Agent, or Firm* — Edwards Wildman Palmer LLP; Joshua L. Jones; Alicia J. Esposito

(57) ABSTRACT

An instrument includes a distraction mechanism having a proximal end and an opposed distal end. The distal end includes opposed first and second end members. A first vertebral endplate spreader includes a proximal spreader section mounted to the first end member of the distraction mechanism. The first spreader also includes a distal spreader section operatively connected to the proximal spreader section for lateral movement relative to the proximal spreader section. A second vertebral endplate spreader is mounted to the second end member of the distraction mechanism. The distraction mechanism is configured and adapted to distract the spreaders apart and to retract the spreaders together along a distraction axis. The distal spreader section of the first spreader is configured to move relative to the second spreader in a lateral direction relative to the distraction axis for correction of vertebral alignment, as in treatment of spondylolisthesis, scoliosis, and the like.

14 Claims, 8 Drawing Sheets

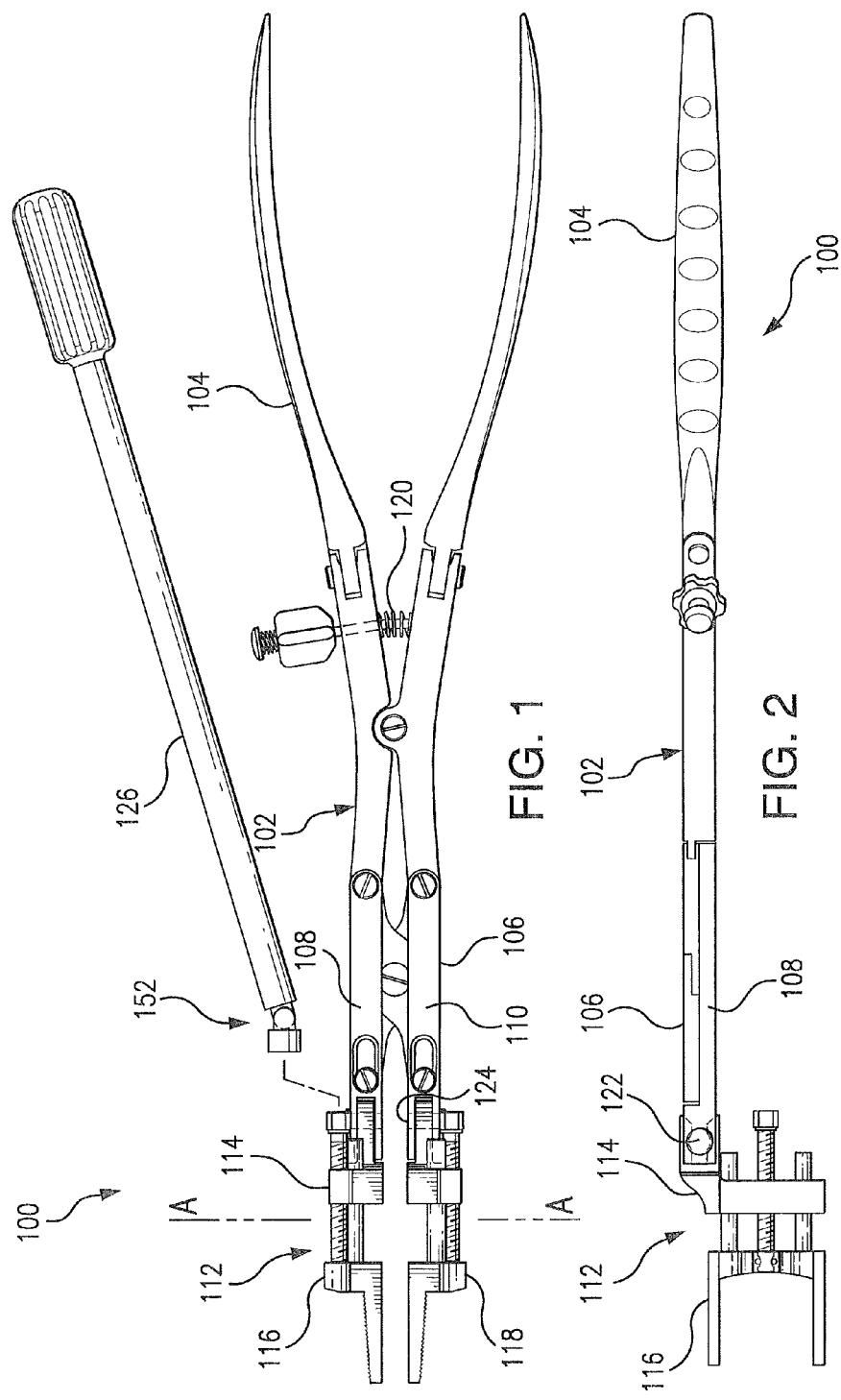

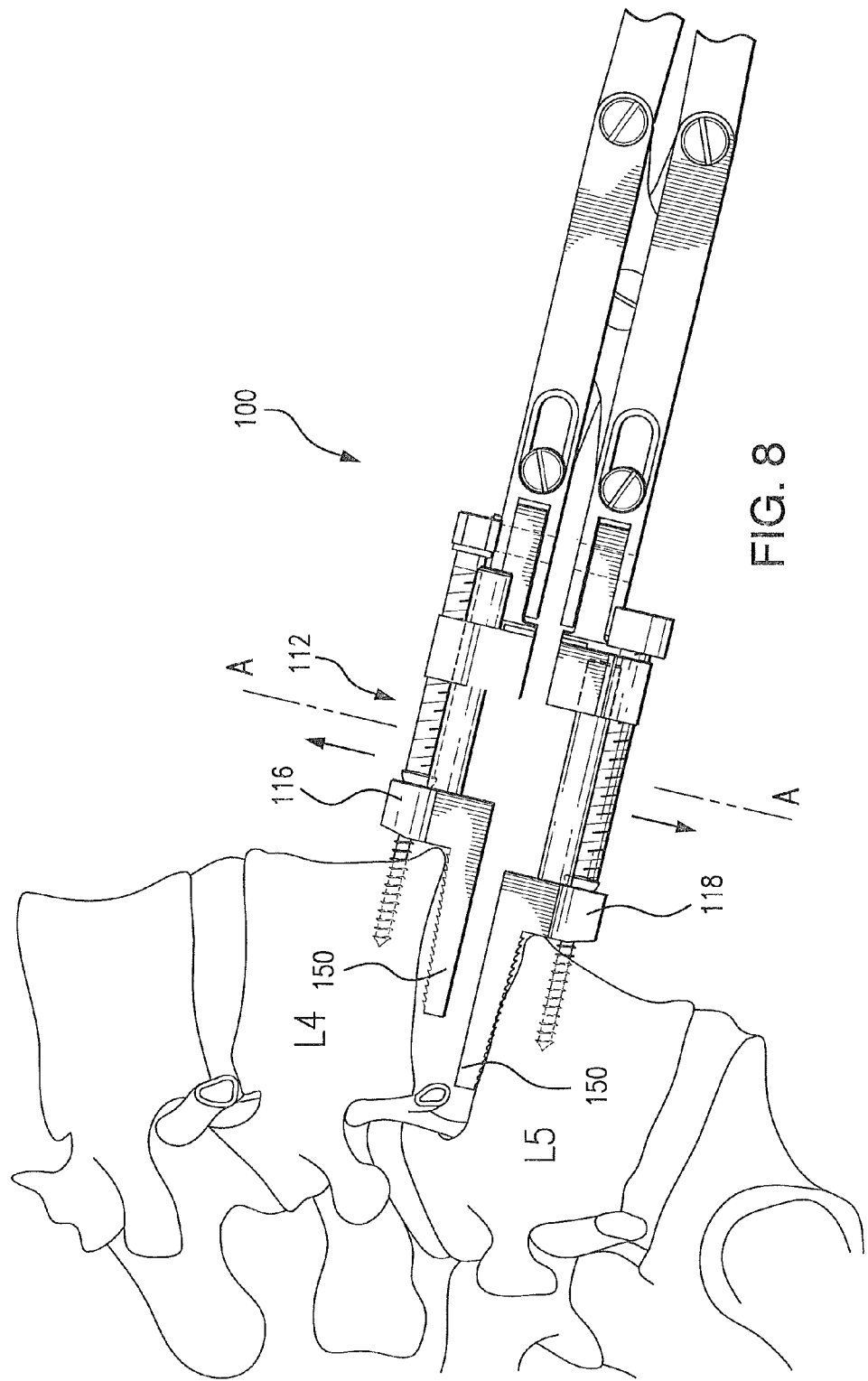

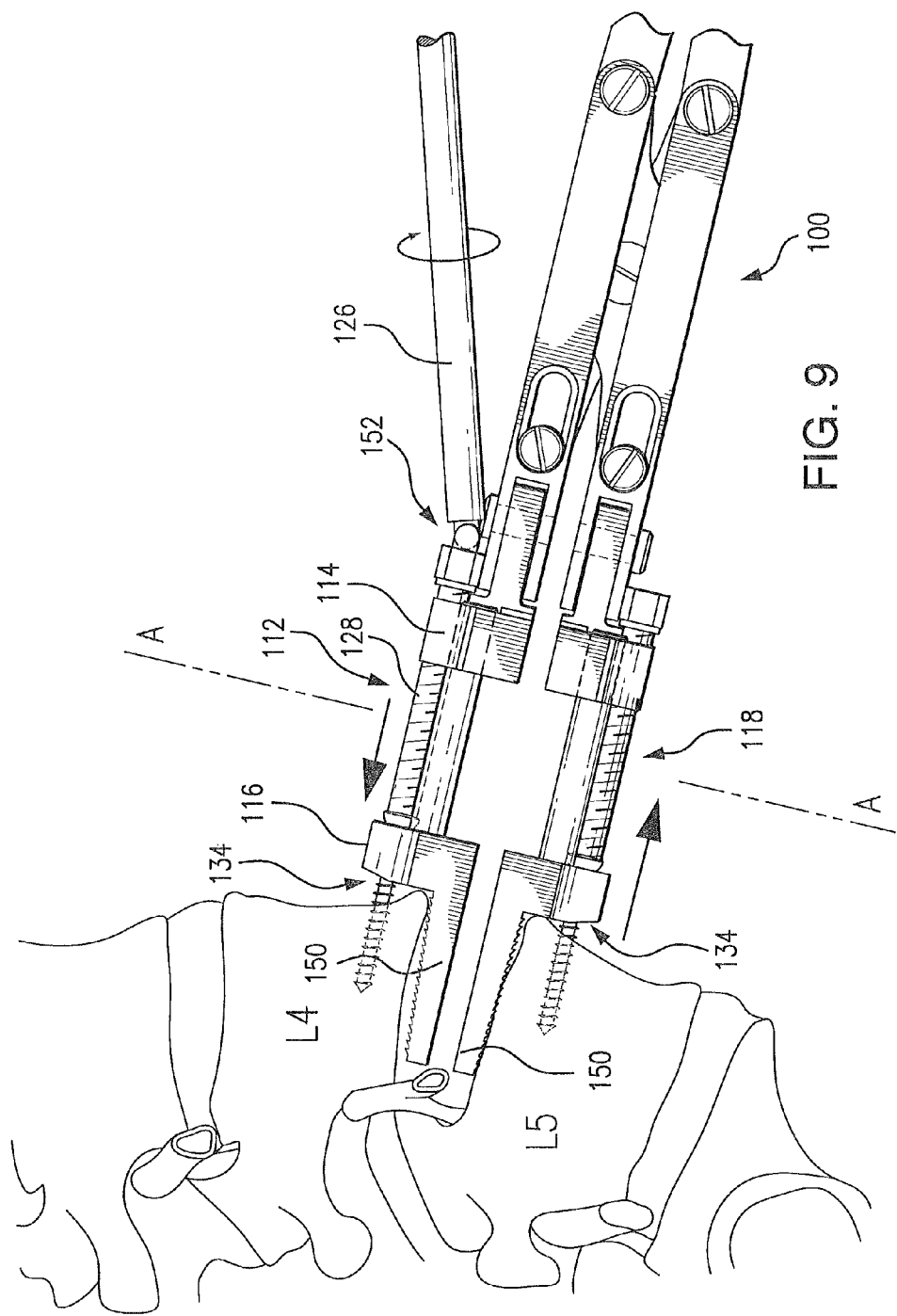

TRANSLATIONAL INSTRUMENTATION FOR SPONDYLOLISTHESIS AND SCOLIOSIS REDUCTION

BACKGROUND OF THE INVENTION

1. Field of the Invention

The present invention relates to instruments and methods of treating spinal conditions, and more particularly to instruments and methods for treating spondylolisthesis, scoliosis, and the like.

2. Description of Related Art

Spondylolisthesis is a spinal disorder that arises from two separate conditions. The first involves a lytic defect in the pars interarticularis, otherwise known as a spondylolysis. The lytic condition most commonly occurs where the lumbar spine meets the sacrum, e.g., at L5-S1. The second condition involves a slippage of the vertebra related to degenerated disc disease and facet arthrosis. The degenerative condition usually involves L4-5 segments. However, spondylolisthesis can occur at any level in the lumbar and less commonly in the cervical spine. Treatment of spondylolisthesis often involves a fusion of the two vertebra involved. Motion sparing technologies, such as total disc replacements, are also used to treat milder cases of degenerative spondylolisthesis.

Spondylolisthesis treatment options routinely include spinal fusion procedures. These can be performed with a combined anterior and posterior approach. The anterior approach is performed via a direct anterior transperitoneal or retroperitoneal approach or lateral approach. This surgery allows direct removal of the majority of the disc, and placement of structural grafts in the disc space. Graft materials include autogenous bone from the iliac crest, allograft, and bone morphogenic protein. The discectomy procedure allows a mobility of the motion segment and enhances fusion rates. This is because anterior grafts are placed under compression as compared to posterior fusion masses, which are under tension. The broad surface area between the endplates allow for higher fusion rates.

The distraction of the collapsed disc space of the listhetic segment allows a mild reduction of the listhesis. This reduction is enhanced by impacting a lordotically shaped graft within the intervertebral space. Alternatively, motion sparing technologies have been used for this problem. Posterior reduction techniques using pedicle screw and rod systems have a significant risk of nerve root traction injuries. None of the traditional instruments, including instruments used in anterior approaches, allow for a combination of both distraction of the disc space and correction of listhesis.

Such conventional methods and systems have generally been considered satisfactory for their intended purpose. However, there is still a need in the art for instrumentation to allow for a combination of distraction of the disc space and correction of the listhesis. There also remains a need in the art for such instrumentation that can be used from anterior and other approaches. The present invention provides a solution for these problems.

SUMMARY OF THE INVENTION

The subject invention is directed to a new and useful instrument for spinal procedures, such as for treating spondylolisthesis, scoliosis, and the like. The instrument includes a distraction mechanism having a proximal end and an opposed distal end. The distal end includes opposed first and second end members. A first vertebral endplate spreader includes a proximal spreader section mounted to the first end member of the distraction mechanism. The first spreader also includes a distal spreader section operatively connected to the proximal spreader section for lateral movement relative to the proximal spreader section. The distal spreader section is configured and adapted to engage a vertebra.

A second vertebral endplate spreader is mounted to the second end member of the distraction mechanism. The second spreader is configured and adapted to engage a vertebra. The distraction mechanism is configured and adapted to distract the spreaders apart and to retract the spreaders together along a distraction axis responsive to action imparted on the proximal end of the distraction mechanism. The distal spreader section of the first spreader is configured to move relative to the second spreader in a lateral direction relative to the distraction axis for correction of vertebral alignment.

In certain embodiments, a pair of guides is provided engaged with the proximal and distal spreader sections to maintain a parallel relationship between the proximal and distal spreader sections during relative lateral travel of the proximal and distal spreader sections. The guides can be mounted to the distal spreader section and can be slideably engaged to the proximal spreader section.

The instrument can include a linear actuator engaged with the proximal and distal spreader sections to actuate relative lateral travel of the proximal and distal spreader sections. The linear actuator can include a threaded screw engaged to threads in the proximal spreader section. The threaded screw can be rotatably engaged with the distal spreader section so rotation of the threaded screw adjusts separation of the proximal and distal spreader sections for relative lateral travel thereof In another aspect, at least one of the proximal and distal spreader sections can include a bone screw passage for accommodating a bone screw to engage the distal spreader section to a vertebra. It is also contemplated that the distal spreader section of the first spreader and the second spreader each include at least one tong for engaging opposed vertebral endplates for distraction of opposed vertebrae.

The invention also provides a method of correcting vertebral alignment. The method includes engaging a distal spreader section of a first vertebral endplate spreader to a first vertebra and engaging a second vertebral endplate spreader to a second vertebra proximate to the first vertebra. The method includes a step of distracting the first and second spreaders apart along a distraction axis to distract the first and second vertebrae from one another. The method also includes translating the distal spreader section of the first spreader relative to the second spreader laterally relative to the distraction axis for correction of alignment of the first and second vertebrae.

The steps of engaging the first and second spreaders to the vertebrae can include approaching the vertebrae with the spreaders from an anterior approach. From such an anterior approach, the step of translating can include moving the superior of the two vertebrae in a posterior direction to correct a listhesis condition of the vertebrae. It is also contemplated that the step of translating can include moving the superior of the two vertebrae in an anterior direction to correct a retrolisthesis condition of the vertebrae.

The steps of engaging the first and second spreaders to the vertebrae can include approaching the vertebrae with the spreaders from a lateral approach. From a lateral approach, the step of translating can include moving the two vertebrae relative to one another in a lateral direction to correct a lateral slippage condition of the vertebrae related to scoliosis.

These and other features of the systems and methods of the subject invention will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the devices and methods of the subject invention without undue experimentation, preferred embodiments thereof will be described in detail herein below with reference to certain figures, wherein:

FIG. 1 is a side elevation view of an exemplary embodiment of an instrument constructed in accordance with the present invention, showing the vertebral endplate spreaders mounted to the distal end of a hand operable mechanism for manipulating the spreaders between distracted and retracted positions, and also showing the driver tool for actuating lateral movement of the distal sections of the upper and lower spreaders;

FIG. 2 is a plan view of the instrument of FIG. 1 without the driver, showing the engagement of the spreaders to the hand operable mechanism;

FIG. 8 is a side elevation view of the instrument of FIG. 1, showing the upper and lower spreaders of the instrument distracting the listhetic vertebrae; and FIG. 9 is a side elevation view of the instrument of FIG. 1, showing the upper and lower spreaders laterally translated relative to one another for correction of the listhesis.

DETAILED DESCRIPTION OF THE PREFERRED EMBODIMENTS

Figure 3:
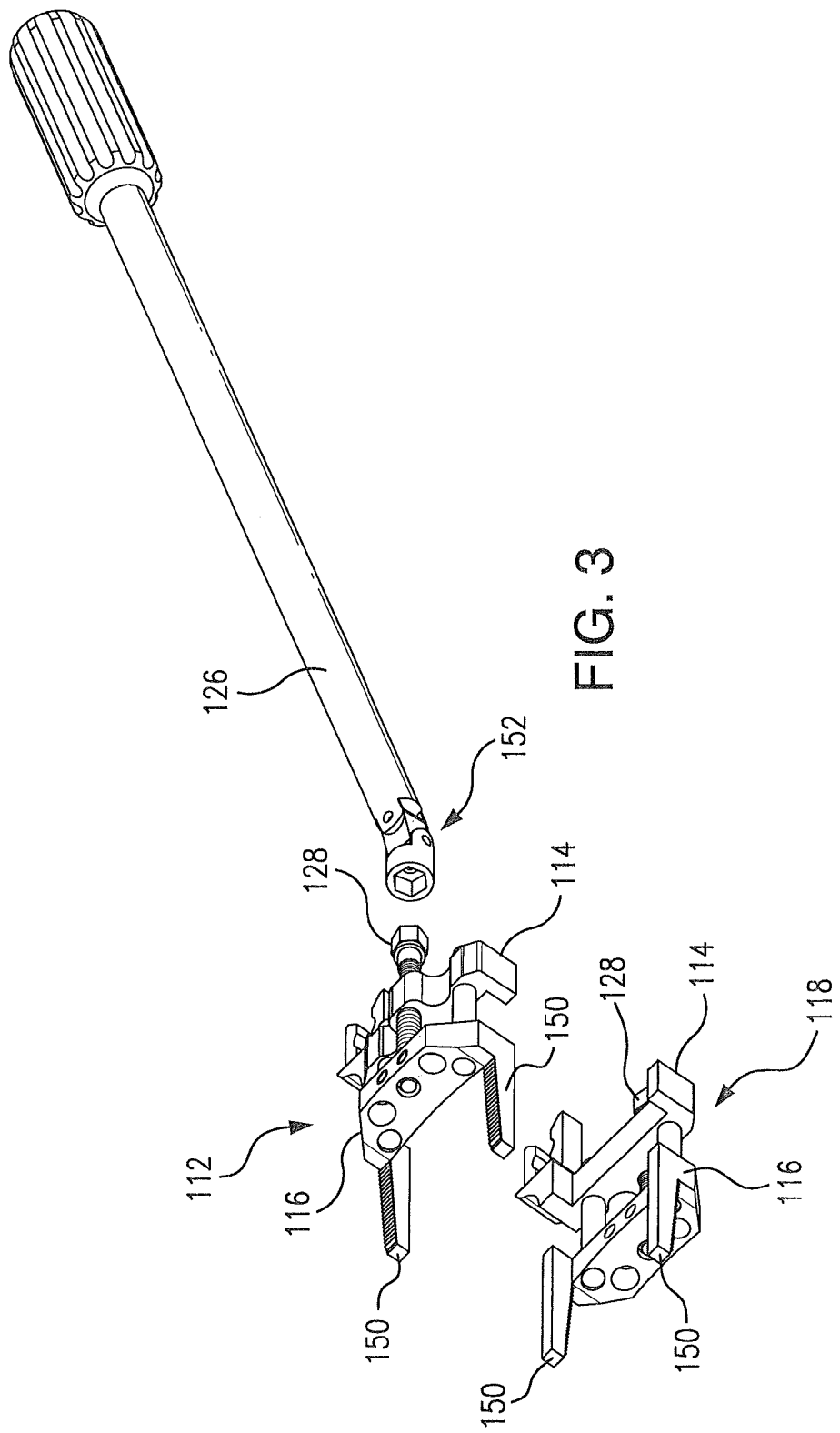
FIG. 3 is an exploded perspective view of the spreaders and driver of FIG. 1, showing the tongs for engaging upper and lower vertebrae.

Reference will now be made to the drawings wherein like reference numerals identify similar structural features or aspects of the subject invention. For purposes of explanation and illustration, and not limitation, a partial view of an exemplary embodiment of an instrument in accordance with the invention is shown in FIG. 1 and is designated generally by reference character 100. Other embodiments of instruments in accordance with the invention, or aspects thereof, are provided in FIGS. 2-9, as will be described. The system of the invention can be used to treat spondylolisthesis, scoliosis, and the like.

Instrument 100 includes a distraction mechanism 102 having a proximal end 104 and an opposed distal end 106. Distal end 106 includes opposed first and second end members 108 and 110, respectively. A first vertebral endplate spreader 112 includes a proximal spreader section 114. Proximal spreader section 114 is mounted to first end member 108 of distraction mechanism 102 by mounting pin 122 shown in FIG. 2. First spreader 112 also includes a distal spreader section 116 operatively connected to proximal spreader section 114 for lateral movement relative to proximal spreader section 114. A second vertebral endplate spreader 118 is mounted to second end member 110 of distraction mechanism 102 by mounting pin 124, which is identified in FIG. 1. The first and second spreaders 112 and 118 are each configured to engage a respective vertebra for correction of vertebral alignment as will be described in greater detail below.

Distraction mechanism 102 is configured and adapted to distract the spreaders 112 and 118 apart from one another and to retract the spreaders 112 and 118 together along a distraction axis A responsive to action imparted on proximal end 104 of distraction mechanism 102. For example, if a user squeezes the handles of proximal end 104, spreaders 112 and 118 will be distracted apart from one another, and if a user allows the handles of proximal end 104 to move apart, for example by action of spring 120, spreaders 112 and 118 will be retracted towards one another.

Referring now to FIG. 3, in addition to being able to move together and apart along distraction axis A, spreaders 112 and 118 can also move laterally with respect to one another, i.e., in a lateral direction relative to distraction axis A. This lateral movement is made possible by the fact that the spreaders 112 and 118 are each split into proximal and distal sections 114 and 116 to vary the offset as needed by the preexisting listhesis. Driver 126 is used to turn actuator screws 128 to actuate the displacement of distal spreader sections 116 relative to proximal spreader sections 114.

Figure 4:
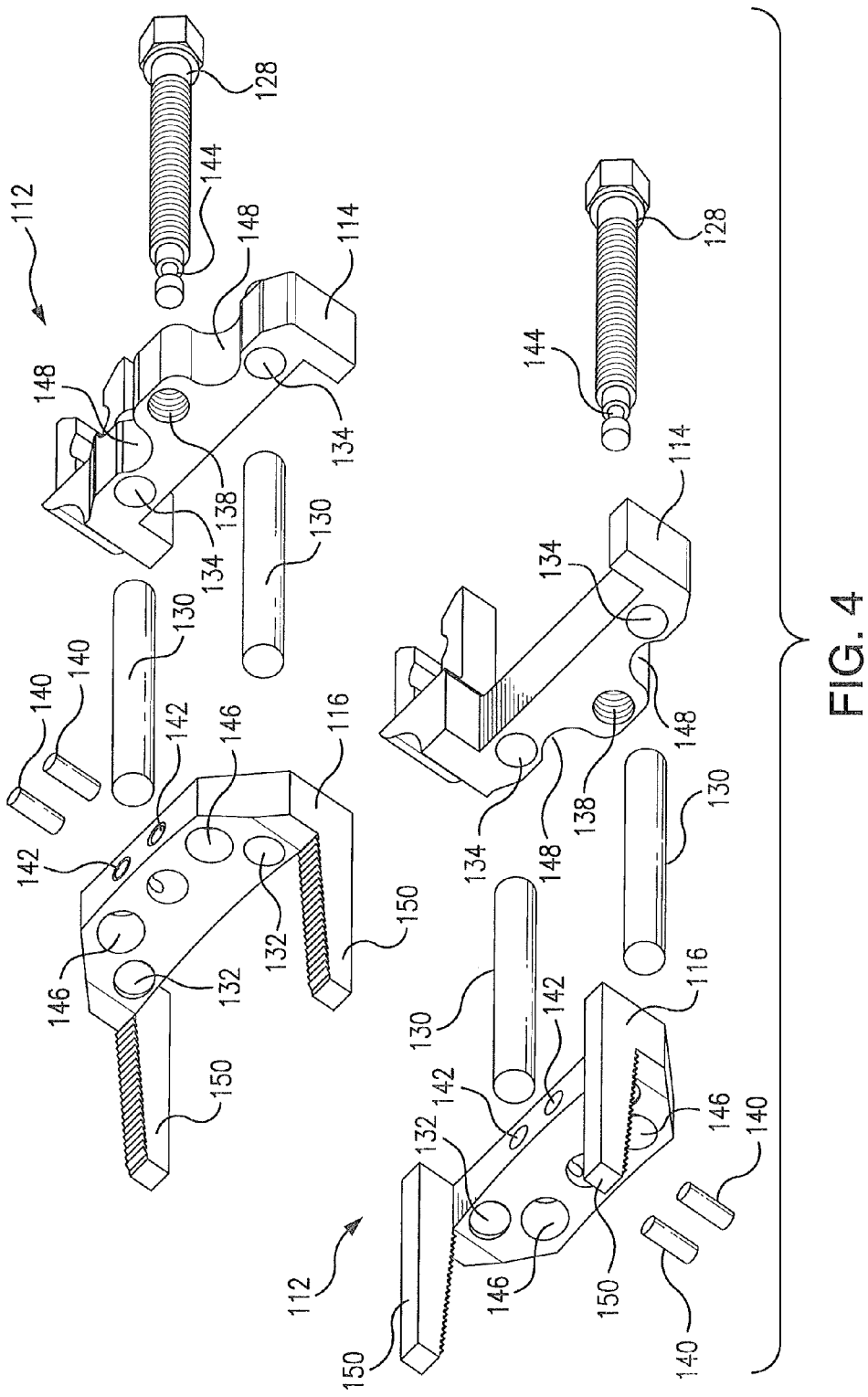
FIG. 4 is an exploded perspective view of the upper and lower spreaders of FIG. 3, showing the separate proximal and distal sections of the each spreader as viewed from above.

Lateral actuation of spreaders 112 and 118 is further described with reference to FIG. 4, which shows parts of spreaders 112 and 118 separated and in the orientation of the procedures described below with reference to FIGS. 5-9. A pair of guides 130 is provided for each spreader 112 and 118, engaged with the proximal and distal spreader sections 114 and 116 to maintain a parallel relationship between the proximal and distal spreader sections 114 and 116 during relative lateral travel thereof. Guides 130 are rigidly mounted in bores 132 of distal spreader sections 116 and are slideably engaged in bores 134 of proximal spreader sections 114.

A linear actuator is provided in each spreader 112 and 118 in the form of actuator screw 128, the threads of which engage with corresponding threads in bore 138 of the respective proximal spreader section 114. Each actuator screw 128 is rotatably engaged to a respective distal spreader section 116, with actuator pins 140 mounted in bores 142 and engaged with groove 144 of each respective actuator screw 128. Rotation of actuator screw 128 adjusts separation of the proximal and distal spreader sections 114 and 116 for relative lateral travel thereof.

Each distal spreader section 116 includes two bone screw bores 146 to provide passages for bone screws to affix each distal spreader section 112 to a respective vertebra. Proximal spreader sections 114 includes bone screw grooves 148 to provide passage for bone screws and any suitable driver device for affixing distal spreader sections 112 to respective vertebra. Each of the distal spreader sections 116 includes a pair of tongs 150 for engaging opposed vertebral endplates for distraction of opposed vertebrae, as described in greater detail below.

Figure 5:
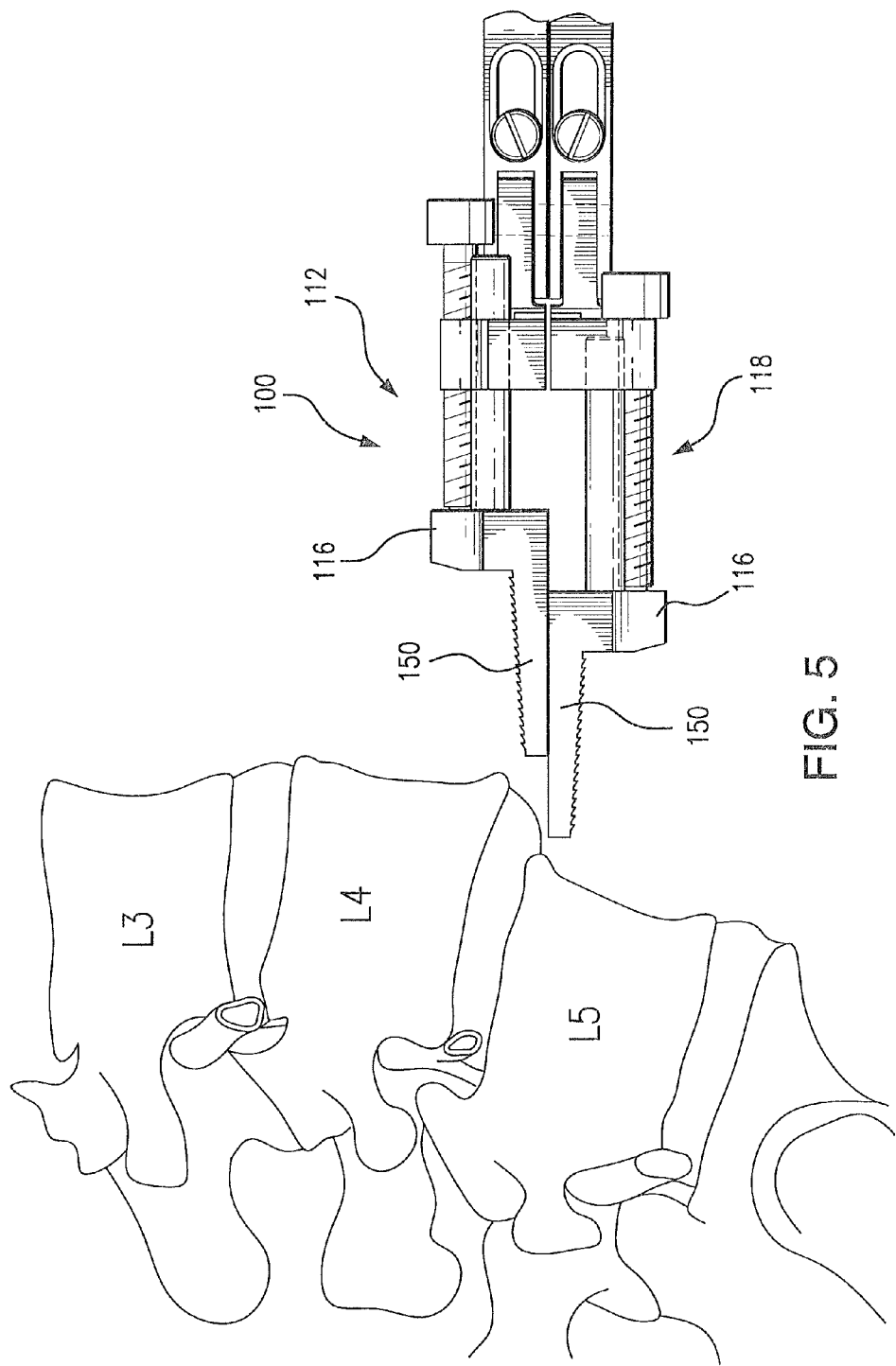
FIG. 5 is a side elevation view of the instrument of FIG. 1, showing the instrument being introduced from an anterior approach to a listhetic pair of lumbar vertebrae.
Figure 6:
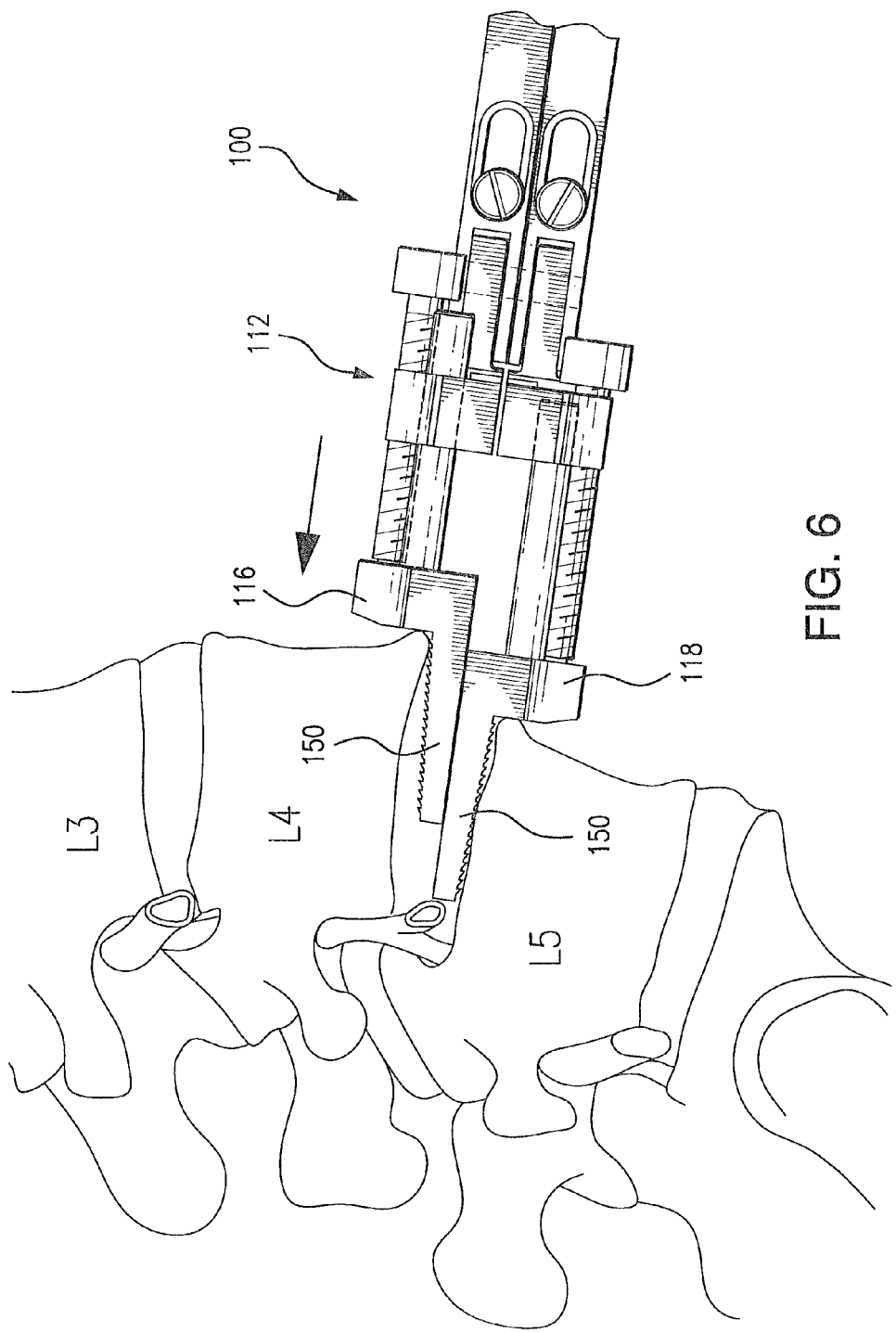
FIG. 6 is a side elevation view of the instrument of FIG. 1, showing the tongs of the instrument being positioned between the listhetic vertebrae.

Referring now to FIGS. 5-9, exemplary methods are described of using instrument 100 for correction of vertebral alignment. FIG. 5 schematically shows instrument 100 approaching listhetic vertebrae L4 and L5 from an anterior approach. The upper or first spreader 112 has its distal spreader section 116 with corresponding tongs 150 in a retracted position. The lower or second spreader 118 has its distal spreader section 116 and corresponding tongs in an advanced position. The relative positions of the upper and lower distal spreader sections 116 corresponds to the offset in alignment of the L4 and L5 vertebrae. As indicated in FIG. 6, tongs 150 of distal spreader section 116 of first spreader 112 are engaged to the listhetic endplate of the L4 vertebra, i.e., the superior or cephalad of the two listhetic vertebrae, and prongs 150 of second spreader 118 are engaged to the adjacent endplate of the L5 vertebra, i.e., the inferior or caudal vertebra.

Figure 7:
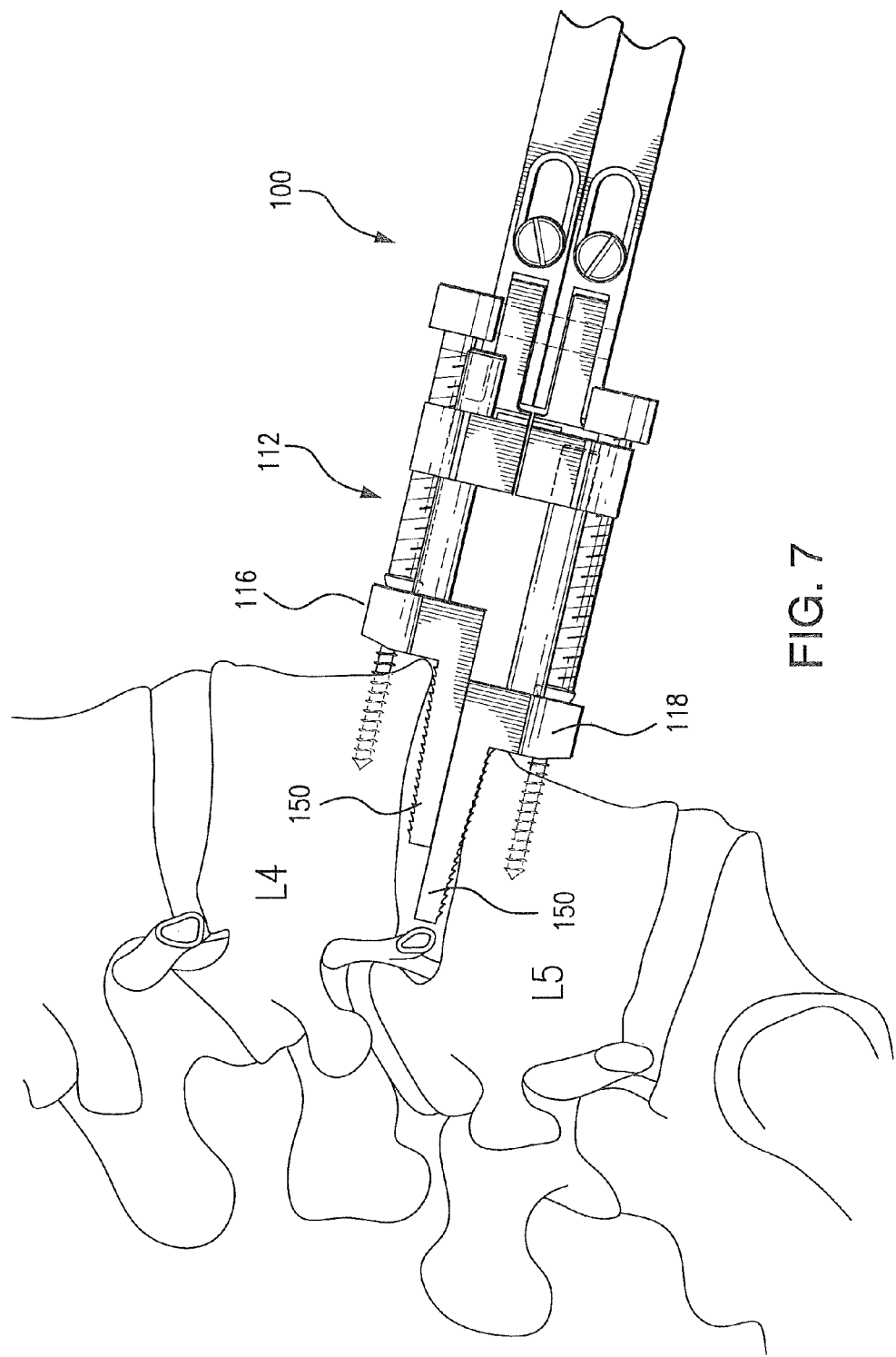
FIG. 7 is a side elevation view of the instrument of FIG. 1, showing the upper and lower spreaders of the instrument mounted to the respective vertebrae.

With instrument 100 engaged with the listhetic vertebrae as shown in FIG. 6, the vertebrae can be distracted apart as shown in FIGS. 8 and 9. FIG. 7 shows bone screws affixing the first and second spreaders 112 and 118 to the respective vertebrae prior to distraction. Those skilled in the art will readily appreciate that one or both spreaders 112 and 118 can be affixed with bone screws before or after distraction without departing from the spirit and scope of the invention. Moreover, bone screw affixation may be omitted for one or both of the spreaders 112 and 118, for example if the forces engaging the respective prongs 150 to the vertebrae provide sufficient fixation without bone screws. Having both spreaders 112 and 118 secured with screws to the respective vertebrae provides extra stability.

With the spreaders 112 and 118 affixed to the respective vertebrae as shown in FIG. 7, the proximal end 104 of distraction mechanism 102 can be actuated to distract the vertebrae along distraction axis A as indicated by the heavy arrows in FIG. 8. With the listhetic vertebrae L4 and L5 distracted, a corpectomy, discectomy, or the like can be performed as needed.

Referring now to FIG. 9, direct posterior translational force is applied after a thorough discectomy and distraction has been performed. In order to correct the listhesis, driver 126 is engaged with actuator screw 128 up upper spreader 112 and turned to spread the upper proximal and distal spreader sections 114 and 116 apart. The actuator screw 128 on lower spreader 118 can also be turned to move the lower distal spreader section 116 in the opposite direction. This action translates the distal spreader sections 116 relative to the proximal spreader sections 114 laterally with respect to distraction axis A for correction of alignment of the L4 and L5 vertebrae. The action of driver 126 and distal spreader sections 116 are indicted by the heavy arrows of FIG. 9. Universal joint 152 accommodates a range of angles of approach for driver 126 for ease of application. Driver 126 is depicted with a female hex head, which those skilled in the art will readily appreciate is exemplary, as any suitable driver/head type or linear actuator type can be used without departing from the spirit and scope of the invention.

During an operation as described above, the surgeon can decide whether a complete or partial reduction of the listhesis should be attempted. After adequate reduction has been achieved, an interbody graft or motion sparing device can be placed through the enhanced slot between the superior and inferior distractor tongs 150. The surgeon can check by direct visualization or intra-operative x-rays as to the vertebral alignment and placement of the interbody graft(s) or motion sparing device. If a fusion is performed, instrument 100 is then removed, including the anterior screws. Supplemental anterior plate fixation can then be applied using the holes previously made in the vertebrae to affix the spreaders 112 and 118. The bores 134 in spreader 112 and corresponding bores 134 in spreader 118 are spaced apart to allow for a corresponding anterior plating system after the reduction has been performed.

Instrument 100 will thus allow a correction of vertebral alignment related to spondylolisthesis. The systems and methods described herein can also be applied for a retrolisthesis, which is a much less common spinal condition. In this case, the lateral motion of distal spreader sections 116 is reversed to be anterior rather than posterior. Furthermore, it is also contemplated that a smaller version of instrument 100 can be used for other applications where smaller size is needed, for example in use on the cervical spine.

In the orientation shown in FIGS. 5-9, first spreader 112 may be referred to as the upper, superior, or cephalad spreader, and second spreader 118 may be referred to as the lower, inferior, or caudal spreader. Those skilled in the art will readily appreciate that while each of the spreaders 112 and 118 is shown and described as split into proximal and distal sections 116 and 114 for lateral movement, it is also possible to use only one split spreader with another spreader that is not split without departing from the spirit and scope of the invention. If both spreaders are split as described above, additional lateral travel is possible compared to embodiments having only one spreader that is split.

While described above in the exemplary context of spondylolisthesis, it is contemplated that other conditions can also be treated using the systems and methods of the invention. For example, there are several forms of scoliosis. These include congenital, idiopathic, and degenerative forms. Deformity of the spine involves a lateral or coronal curvature of the spine. In the lumbar spine, especially in degenerative scoliosis, there is often a lateral slippage of one vertebra relative to another. The instrumentation described above to reduce an anterior spondylolisthesis can be used in a lateral approach on the convexity of the curve to reduce the scoliosis and at the same time allow intervertebral distraction. An instrument adapted from instrument 100 for treating scoliosis or similar applications can be of a smaller diameter and can have one prong on each of the spreaders instead of the two prongs 150 shown and described above.

The methods and instruments described herein advantageously allow for both distraction and relative lateral repositioning of vertebrae. Additional advantages include allowing for disc space distraction which enhances foraminal height. This increased foraminal height reduces the potential for nerve root entrapment during a reduction of the listhesis.

The methods and systems of the present invention, as described above and shown in the drawings, provide for methods and instruments for correcting misalignment of vertebrae with superior properties including distracting and laterally repositioning vertebrae with the same instrument. While the apparatus and methods of the subject invention have been shown and described with reference to preferred embodiments, those skilled in the art will readily appreciate that changes and/or modifications may be made thereto without departing from the spirit and scope of the subject invention.

What is claimed is:

1. An instrument for spinal procedures comprising:
a distraction mechanism having a proximal end and an opposed distal end, wherein the distal end includes opposed first and second end members;
a first vertebral endplate spreader including a proximal spreader section mounted to the first end member of the distraction mechanism, and including a distal spreader section operatively connected to the proximal spreader section for movement in a lateral direction relative to the proximal spreader section, wherein the distal spreader section is configured and adapted to engage a first vertebra; a second vertebral endplate spreader mounted to the second end member of the distraction mechanism, the second spreader being configured and adapted to engage a second vertebra, wherein the distraction mechanism is configured and adapted to distract the spreaders apart and to retract the spreaders together along a distraction axis responsive to action imparted on the proximal end of the distraction mechanism, and wherein the distal spreader section of the first spreader is configured to move relative to the second spreader in the lateral direction relative to the distraction axis for correction of vertebral alignment by moving at least one of the first and second vertebrae in the lateral direction, wherein the lateral direction is substantially orthogonal to the distraction axis;

a linear actuator engaged with the proximal and distal spreader sections to actuate relative travel of the proximal and distal spreader sections; and a pair of guides each directly engaged with the proximal and distal spreader sections to maintain a parallel relationship between the proximal and distal spreader sections during relative lateral travel of the proximal and distal spreader sections, each guide disposed on respective opposing sides of the linear actuator, wherein the guides are mounted to one of the distal spreader section and the proximal spreader section and are slideably engaged to the other non-mounted section.

2. An instrument as recited in claim 1, wherein the guides are mounted to the distal spreader section and are slideably engaged to the proximal spreader section.

3. An instrument as recited in claim 1, wherein the linear actuator includes a threaded screw engaged to threads in the proximal spreader section, and rotatably engaged with the distal spreader section so rotation of the threaded screw adjusts separation of the proximal and distal spreader sections for relative lateral travel thereof.

4. An instrument as recited in claim 1, wherein at least one of the proximal and distal spreader sections includes a bone screw passage for accommodating a bone screw to engage the distal spreader section to a vertebra.

5. An instrument as recited in claim 1, wherein the distal spreader section of the first spreader and the second spreader each include at least one tong for engaging opposed vertebral endplates for distraction of opposed vertebrae.

6. An instrument for spinal procedures comprising:
a distraction mechanism having a proximal end and an opposed distal end, wherein the distal end includes opposed first and second end members;
a first vertebral endplate spreader including a proximal spreader section mounted to the first end member of the distraction mechanism, and including a distal spreader section operatively connected to the proximal spreader section for movement in a lateral direction relative to the proximal spreader section, wherein the distal spreader section is configured and adapted to engage a first vertebra; a second vertebral endplate spreader mounted to the second end member of the distraction mechanism, the second spreader being configured and adapted to engage a second vertebra, wherein the distraction mechanism is configured and adapted to distract the spreaders apart and to retract the spreaders together along a distraction axis responsive to action imparted on the proximal end of the distraction mechanism, and wherein the distal spreader section of the first spreader is configured to move relative to the second spreader in the lateral direction relative to the distraction axis for correction of vertebral alignment by moving at least one of the first and second vertebrae in the lateral direction, wherein the lateral direction is substantially orthogonal to the distraction axis;

a linear actuator engaged with the proximal and distal spreader sections to actuate relative travel of the proximal and distal spreader sections; and a pair of guides each directly engaged with the proximal and distal spreader sections to maintain a parallel relationship between the proximal and distal spreader sections during relative lateral travel of the proximal and distal spreader sections, each guide disposed on respective opposing sides of the linear actuator, wherein the guides are mounted to the distal spreader section and are slideably engaged to the proximal spreader section.

7. An instrument as recited in claim 6, wherein the linear actuator includes a threaded screw engaged to threads in the proximal spreader section, and rotatably engaged with the distal spreader section so rotation of the threaded screw adjusts separation of the proximal and distal spreader sections for relative lateral travel thereof.

8. An instrument as recited in claim 6, wherein at least one of the proximal and distal spreader sections includes a bone screw passage for accommodating a bone screw to engage the distal spreader section to a vertebra.

9. An instrument as recited in claim 6, wherein the distal spreader section of the first spreader and the second spreader each include at least one tong for engaging opposed vertebral endplates for distraction of opposed vertebrae.

10. An instrument for spinal procedures comprising:
a distraction mechanism having a proximal end and an opposed distal end, wherein the distal end includes opposed first and second end members;
a first vertebral endplate spreader including a proximal spreader section mounted to the first end member of the distraction mechanism, and including a distal spreader section operatively connected to the proximal spreader section for movement in a lateral direction relative to the proximal spreader section, wherein the distal spreader section is configured and adapted to engage a first vertebra; a second vertebral endplate spreader mounted to the second end member of the distraction mechanism, the second spreader being configured and adapted to engage a second vertebra, wherein the distraction mechanism is configured and adapted to distract the spreaders apart and to retract the spreaders together along a distraction axis responsive to action imparted on the proximal end of the distraction mechanism, and wherein the distal spreader section of the first spreader is configured to move relative to the second spreader in the lateral direction relative to the distraction axis for correction of vertebral alignment by moving at least one of the first and second vertebrae in the lateral direction, wherein the lateral direction is substantially orthogonal to the distraction axis;

a linear actuator engaged with the proximal and distal spreader sections to actuate relative travel of the proximal and distal spreader sections; and a pair of guides each directly engaged with the proximal and distal spreader sections to maintain a parallel relationship between the proximal and distal spreader sections during relative lateral travel of the proximal and distal spreader sections, each guide disposed on respective opposing sides of the linear actuator, wherein the proximal and distal spreader sections are not directly threaded to one another.

11. An instrument as recited in claim 10, wherein the guides are mounted to the distal spreader section and are slideably engaged to the proximal spreader section.

12. An instrument as recited in claim 10, wherein the linear actuator includes a threaded screw engaged to threads in the proximal spreader section, and rotatably engaged with the distal spreader section so rotation of the threaded screw adjusts separation of the proximal and distal spreader sections for relative lateral travel thereof.

13. An instrument as recited in claim 10, wherein at least one of the proximal and distal spreader sections includes a bone screw passage for accommodating a bone screw to engage the distal spreader section to a vertebra.

14. An instrument as recited in claim 10, wherein the distal spreader section of the first spreader and the second spreader each include at least one tong for engaging opposed vertebral endplates for distraction of opposed vertebrae.

* * * * *